United States Patent
Morcos

(10) Patent No.: US 11,446,840 B2
(45) Date of Patent: *Sep. 20, 2022

(54) ACCESSORY FOR OSCILLATING POWER TOOL

(71) Applicant: Universal Arbor LLC, Dallas, TX (US)

(72) Inventor: Cherif Morcos, Kirkland (CA)

(73) Assignee: Universal Arbor LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/170,757

(22) Filed: Feb. 8, 2021

(65) Prior Publication Data

US 2021/0154877 A1 May 27, 2021

Related U.S. Application Data

(63) Continuation of application No. 16/273,512, filed on Feb. 12, 2019, now Pat. No. 10,953,563, which is a continuation of application No. 15/238,491, filed on Aug. 16, 2016, now Pat. No. 10,245,744, which is a continuation of application No. 12/932,728, filed on Mar. 7, 2011, now abandoned.

(60) Provisional application No. 61/316,294, filed on Mar. 22, 2010.

(51) Int. Cl.
*B26D 7/26* (2006.01)
*A61B 17/14* (2006.01)

(52) U.S. Cl.
CPC ............... *B26D 7/26* (2013.01); *A61B 17/14* (2013.01)

(58) Field of Classification Search
CPC ... Y10T 83/9377; Y10T 83/9379; B26D 7/26; B26D 7/2614; B26D 17/147; A61B 17/14; A61B 17/142
USPC ............................ 30/394, 393; 606/176, 178
See application file for complete search history.

(56) References Cited

U.S. PATENT DOCUMENTS

| | | |
|---|---|---|
| 2,198,444 A | 4/1940 | Swanson |
| 3,103,069 A | 9/1963 | Gary |
| 4,058,317 A | 11/1977 | McCarthy |
| 4,637,391 A | 1/1987 | Schlein |
| 4,657,428 A | 4/1987 | Wiley |
| 5,048,366 A | 9/1991 | Spanio |
| D343,247 S | 1/1994 | Walen |
| 5,306,285 A | 4/1994 | Miller |
| 5,489,285 A | 2/1996 | Goris |
| 5,496,316 A | 3/1996 | Goris |
| 5,694,693 A | 12/1997 | Hutchins |
| 5,735,866 A | 4/1998 | Adams |
| 7,189,239 B2 | 3/2007 | Fisher |
| 7,217,177 B2 | 5/2007 | French et al. |
| D633,928 S | 3/2011 | Nilsson et al. |
| D651,062 S | 12/2011 | Wackwitz |
| D651,799 S | 1/2012 | Tong |
| D651,874 S | 1/2012 | Davidian et al. |
| D651,875 S | 1/2012 | Davidian et al. |

(Continued)

*Primary Examiner* — Phong H Nguyen
(74) *Attorney, Agent, or Firm* — Cecil Law PLLC

(57) ABSTRACT

An accessory for an oscillating power tool is provided. The accessory has a body with an arbor for attaching to the oscillating power tool. The arbor comprises a plurality of primary and secondary openings. The primary openings extend radially from the central axis of the arbor. The secondary openings are also dispersed around the central axis. The accessory can fit, with no loss of functionality, oscillating power tools' connectors from multiple manufacturers.

20 Claims, 6 Drawing Sheets

(56) References Cited

U.S. PATENT DOCUMENTS

| | | |
|---|---|---|
| D651,876 S | 1/2012 | Davidian et al. |
| D651,877 S | 1/2012 | Davidian et al. |
| D651,878 S | 1/2012 | Davidian et al. |
| D652,274 S | 1/2012 | Davidian et al. |
| D677,546 S | 3/2013 | Zhou et al. |
| D682,652 S | 5/2013 | McRoberts et al. |
| D693,193 S | 11/2013 | Bozic |
| D694,076 S | 11/2013 | Davidian et al. |
| D694,077 S | 11/2013 | Bozic |
| D694,596 S | 12/2013 | Davidian et al. |
| D694,597 S | 12/2013 | Davidian et al. |
| D694,598 S | 12/2013 | Davidian et al. |
| D694,599 S | 12/2013 | Davidian et al. |
| D697,384 S | 1/2014 | Wackwitz |
| D709,341 S | 7/2014 | Nispel |
| 8,950,756 B2 | 2/2015 | Lu et al. |
| D724,923 S | 3/2015 | McRoberts et al. |
| D735,568 S | 8/2015 | Barnett |
| D741,135 S | 10/2015 | Yang et al. |
| D741,136 S | 10/2015 | Yang et al. |
| 9,186,770 B2 | 11/2015 | Montplaisir et al. |
| D744,800 S | 12/2015 | Cooksey et al. |
| D750,461 S | 3/2016 | McRoberts et al. |
| 2002/0070037 A1 | 6/2002 | Jasch |
| 2002/0112589 A1 | 8/2002 | Lee et al. |
| 2004/0098000 A1 | 5/2004 | Kleinwaechter |
| 2006/0150428 A1 | 7/2006 | Baculy |
| 2008/0190259 A1 | 8/2008 | Bohne |
| 2010/0056029 A1 | 9/2010 | Grunikiewicz |
| 2011/0076927 A1 | 3/2011 | Ho |
| 2011/0277611 A1 | 11/2011 | Chen et al. |
| 2011/0316241 A1 | 12/2011 | Zhang et al. |
| 2011/0316242 A1 | 12/2011 | Zhang et al. |
| 2012/0170976 A1 | 7/2012 | Cai |
| 2012/0311876 A1 | 12/2012 | Zhang |
| 2014/0190328 A1 | 7/2014 | Karlen |

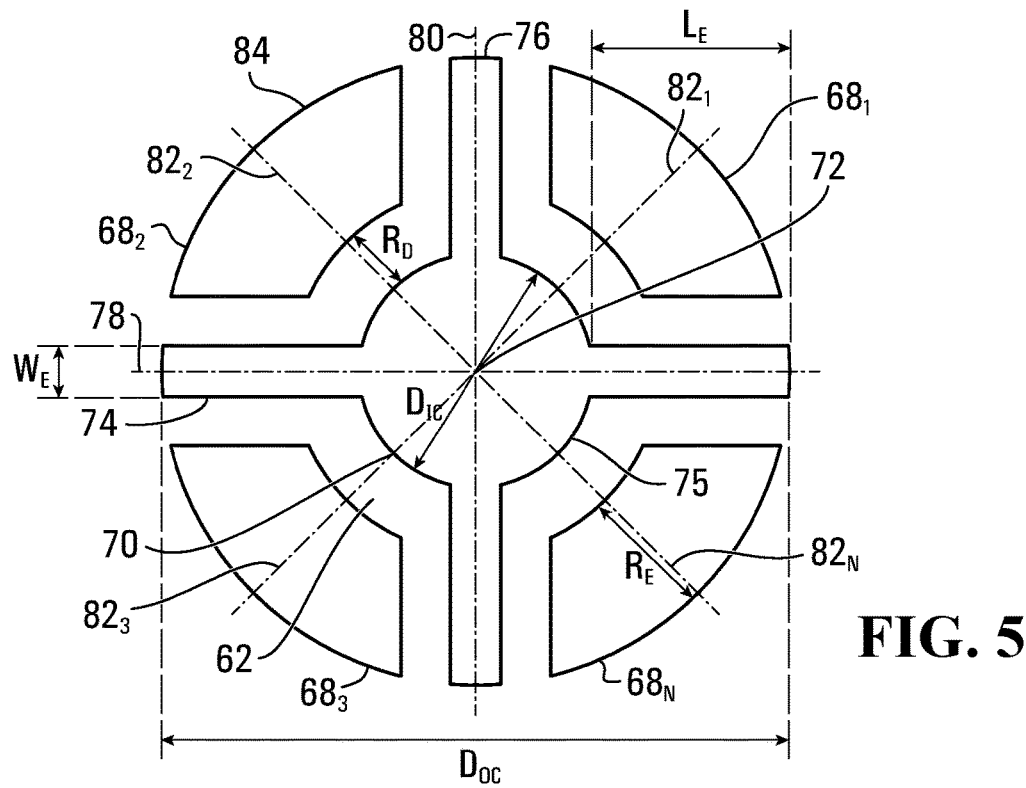
FIG. 5
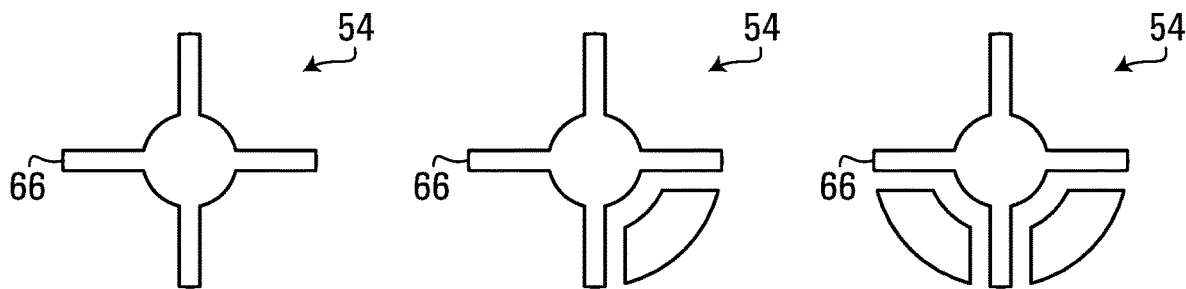
FIG. 6A  FIG. 6B  FIG. 6C
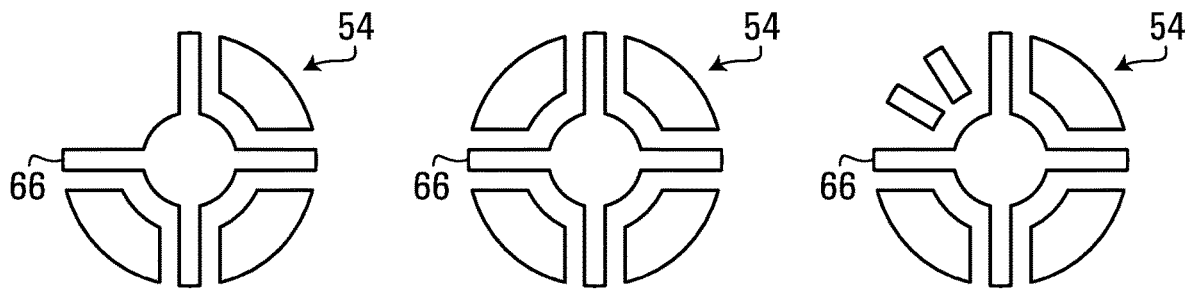
FIG. 6D  FIG. 6E  FIG. 6F

ACCESSORY FOR OSCILLATING POWER TOOL

CROSS REFERENCE TO RELATED APPLICATIONS

This application is a continuation claiming the benefit of priority under 35 U.S.C. § 120 based on U.S. patent application Ser. No. 16/273,512, which was filed on Feb. 12, 2019, which itself claim the benefit of priority under 35 U.S.C. § 120 based on U.S. patent application Ser. No. 15/238,491, (now patented as U.S. Pat. No. 10,245,744) which was filed on Aug. 16, 2016, which itself claimed the benefit of priority under 35 U.S.C. § 120 based on U.S. patent application Ser. No. 12/932,728, which was filed on Mar. 7, 2011, which itself claimed the benefit of priority under 35 USC 119(e) based on U.S. Provisional Patent Application No. 61/316,294 filed on Mar. 22, 2010. The contents of each of these aforementioned applications are incorporated herein by reference in their entirety.

FIELD OF THE INVENTION

The invention relates generally to accessories for power tools, and more particularly, to accessories such as blades, rasps, sanders, scrapers and the like that can be secured to a drive flange of oscillating power tools for use therewith.

BACKGROUND

Oscillating power tools may be used in combination with different types of accessories (e.g., blades, rasps, sanders, scrapers) in order to perform different desired tasks. The accessories are typically configured to be releasably fastened to and removed from the oscillating power tool to either replace a used accessory with a newer one and/or to attach a different type of accessary to the oscillating power tool to perform a different function. Manufacturers of these oscillating power tools often sell such accessories with the caveat that the accessories are specifically designed for exclusive use with their brand of oscillating power tool and are therefore incompatible with other manufacturers' oscillating power tools.

This may be more easily understood with reference to a specific example.

U.S. Patent Application Publication 2008/0190259 to Bohne ("Bohne"), which is part of the prior art, describes an example of a prior art accessory 14 (e.g., a blade) mountable to an oscillating power tool 28, as shown in FIGS. 1A and 1B. More specifically, as is common for oscillating power tools, the accessory 14 is mounted to a drive flange 38 of the oscillating power tool 28 via a fastening portion 44 of the accessory 14 which has a number of form-locking elements 12' (i.e., openings) for engaging a number of form-locking elements 12 (i.e., projections) of the drive flange 38. Once the accessory 14 is engaged with the drive flange 38 in that manner, a screw 42 is engaged with a threaded hole 10 of the drive flange 38 to clamp the accessory 14 against the drive flange 38.

In order to ensure that only their accessories are compatible with their oscillating power tools, manufacturers configure the projections on the drive flanges of their oscillating power tools (such as the form-locking elements 12 of Bohne) to have a specific pattern with which only their respective accessories are matable. As a result, users that own oscillating power tools made by different manufacturers are required to hold stock of each individual oscillating power tool's requisite replacement accessories due to the accessories' respective arbor (i.e., a fitting slot/hole—such as the form-locking elements 12' of Bohne) that is unique to each manufacturer. This results in high inventories of blades and/or other types of accessories which can be costly to maintain, particularly since some accessories, such as blades, provided by these manufacturers are expensive. Moreover and in particular with respect to blades, due to this high associated cost, users tend to stretch the use of manufacturers' blades beyond a point of usefulness (i.e., after they've become dull).

In light of the above, it is apparent that there is a need in the industry to provide blades and other accessories for oscillating power tools which are compatible with oscillating power tools made by different manufacturers.

SUMMARY

In accordance with a first aspect, a blade accessory for use with an oscillating power tool is provided. The blade accessory comprises a body extending in a longitudinal direction from a first end to a second end. The first end of the body is a blade end for cutting and the second end of the body is an attachment end for mounting the blade accessory to the oscillating power tool. The blade accessory also comprises an arbor defined at the attachment end of the body. The arbor is configured to matingly engage attachment elements of a drive flange of the oscillating power tool. The arbor comprises a plurality of openings including a primary opening which comprises: a central opening which defines a central axis of the arbor; a first elongated opening conjoined with the central opening and extending radially from the central axis along a first radial axis; and a second elongated opening conjoined with the central opening and extending radially from the central axis along a second radial axis. The second radial axis is substantially orthogonal to the first radial axis. The plurality of openings further includes a set of secondary openings disjoined from the primary opening and positioned radially about the central axis along respective radial axes distinct from the first and second radial axes.

In accordance with another aspect, an accessory for use with an oscillating power tool is provided. The accessory comprises a body having a functional portion for performing work and an attachment portion for mounting the accessory to the oscillating power tool. The accessory further comprises an arbor defined at the attachment portion of the body. The arbor is configured to matingly engage attachment elements of a drive flange of the oscillating power tool. The arbor comprises a plurality of openings including a primary opening which comprises: a central opening defining a central axis of the arbor; a first elongated opening conjoined with the central opening and extending radially from the central axis along a first radial axis; and a second elongated opening conjoined with the central opening and extending radially from the central axis along a second radial axis. The second radial axis 1s substantially orthogonal to the first radial axis. The plurality of openings further includes a set of secondary openings disjoined from the primary opening and positioned radially about the central axis along respective radial axes.

In accordance with another aspect, an accessory for use with an oscillating power tool is provided. The accessory comprises a body having a functional portion for performing work and an attachment portion for mounting the accessory to the oscillating power tool. The accessory further comprises an arbor defined at the attachment portion of the body. The arbor is configured to matingly engage attachment elements of a drive flange of the oscillating power tool. The arbor comprises a plurality of cavities including a primary cavity which comprises: a central cavity defining a central axis of the arbor; a first elongated cavity conjoined with the central opening and extending radially from the central axis along a first radial axis; and a second elongated cavity conjoined with the central cavity and extending radially from the central axis along a second radial axis. The second radial axis is substantially orthogonal to the first radial axis. The plurality of cavities further includes a set of secondary cavities disjoined from the primary cavity and positioned radially about the central axis along respective radial axes.

The arbor of the blade or other accessory presented here differs from previously used arbors because it can fit, with no loss of functionality, the drive flange of oscillating power tools made by many major manufacturers.

The arbor may be used in connection with blades, rasps, sanders, scrapers or any other attachment for power oscillating tools in any material such as metal, plastic, or other. The cavities of the arbor are defined in order to fit many of the major power oscillating tool manufacturer's devices.

The arbor includes opening and/or embossed/de-bossed portions that allow for attachments made of metal, plastic, or other, to fit onto the oscillating power tool's drive flange. The end of the attachment can serve as either a blade to cut, a sander to sand, a rasp to sand, a scraper to scrape, or a grout remover to remove grout with power assistance from the power oscillating tool. The attachment fits tightly to provide functionality, maintain torque, and is secured by the arbor, and a screw or fastener on the other side of the drive flange.

Other aspects of the invention include design components that make the accessory comprising the arbor unique. The above summary of the present disclosure is not intended to describe every implementation of the present disclosure. The figures and the detailed description that follow more particularly exemplify these implementations.

BRIEF DESCRIPTION OF THE DRAWINGS

FIG. 5 is a diagrammatic view of an arbor of the blade of FIG. 4 in which the arbor comprises a plurality of cavities, including a primary cavity and a set of secondary cavities;

FIG. 6A shows a variant of the arbor of FIG. 4 in which the plurality of cavities of the arbor includes a primary cavity but no secondary cavities;

FIG. 6B shows another variant of the arbor of FIG. 4 in which the set of secondary cavities includes one secondary cavity;

FIG. 6C shows another variant of the arbor of FIG. 4 in which the set of secondary cavities includes two secondary cavities;

FIG. 6D shows another variant of the arbor of FIG. 4 in which the set of secondary cavities includes three secondary cavities;

FIG. 6E shows another variant of the arbor of FIG. 4 in which the set of secondary cavities includes four secondary cavities;

FIG. 6F shows another variant of the arbor of FIG. 4 in which the set of secondary cavities includes five secondary cavities;

Figure 1A:
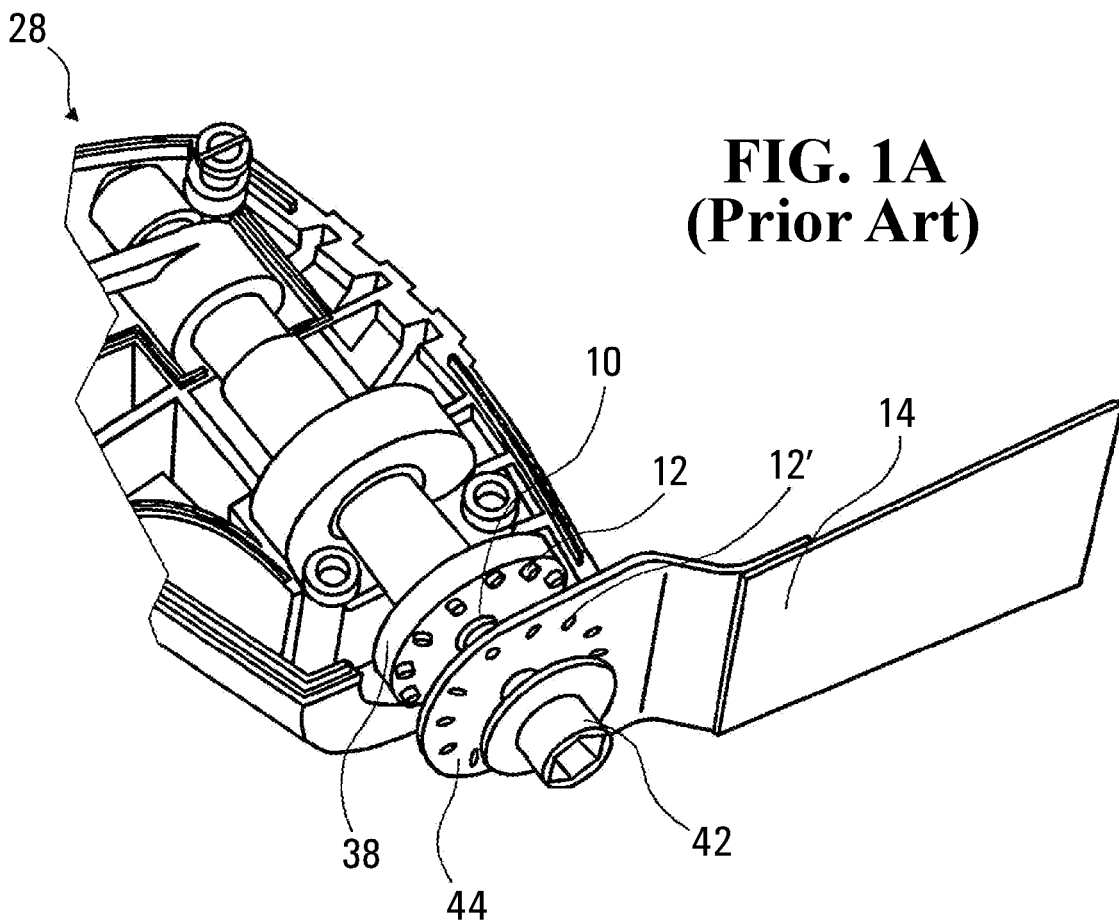
FIG. 1A shows a prior art accessory being mounted to a drive flange of an oscillating power tool.
Figure 1B:
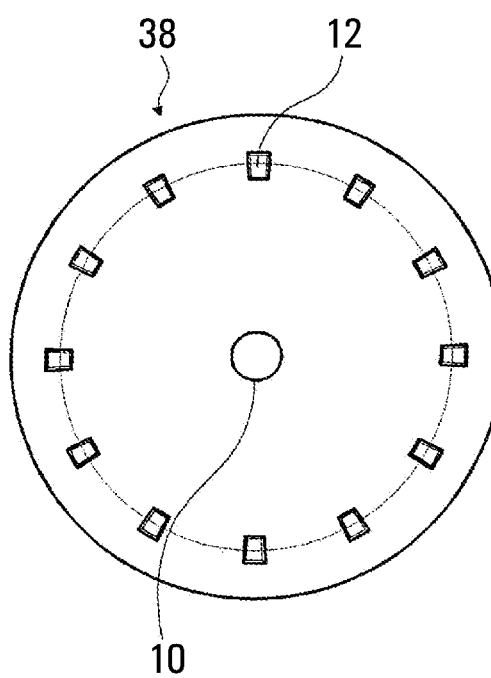
FIG. 1B shows a pattern of projections defined in the drive flange of the oscillating power tool shown in FIG. 1A.

In the drawings, embodiments of the invention are illustrated by way of examples. It is to be expressly understood that the description and drawings are only for the purpose of illustration and are an aid for understanding. They are not intended to be a definition of the limits of the invention.

DETAILED DESCRIPTION

Figure 2A:
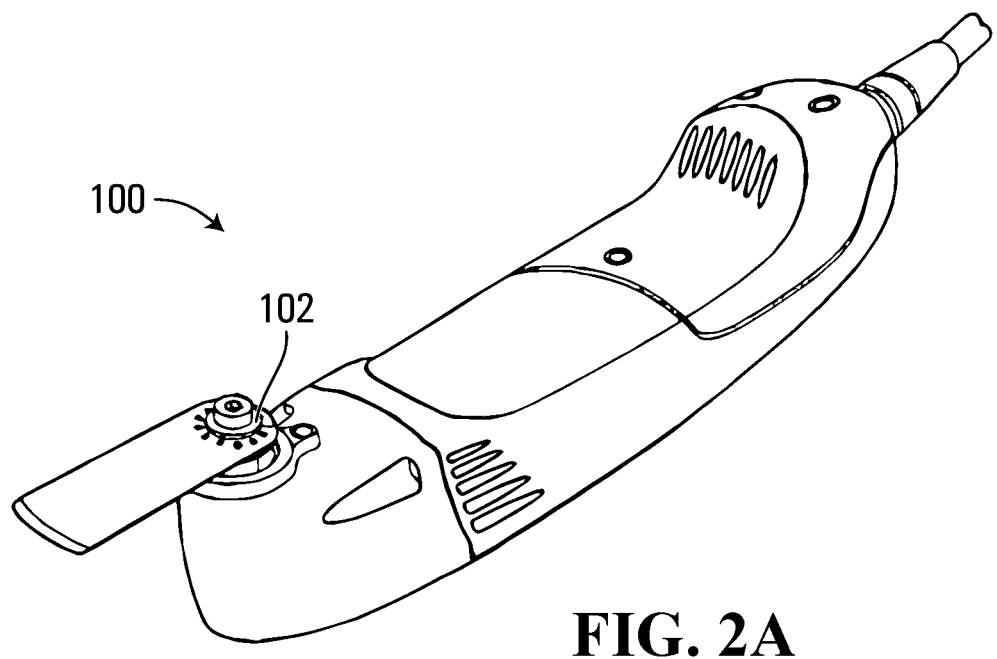
FIGS. 2A and 2B show top and bottom perspective views of another example of an oscillating power tool to which is mounted another prior art accessory.
Figure 2B:
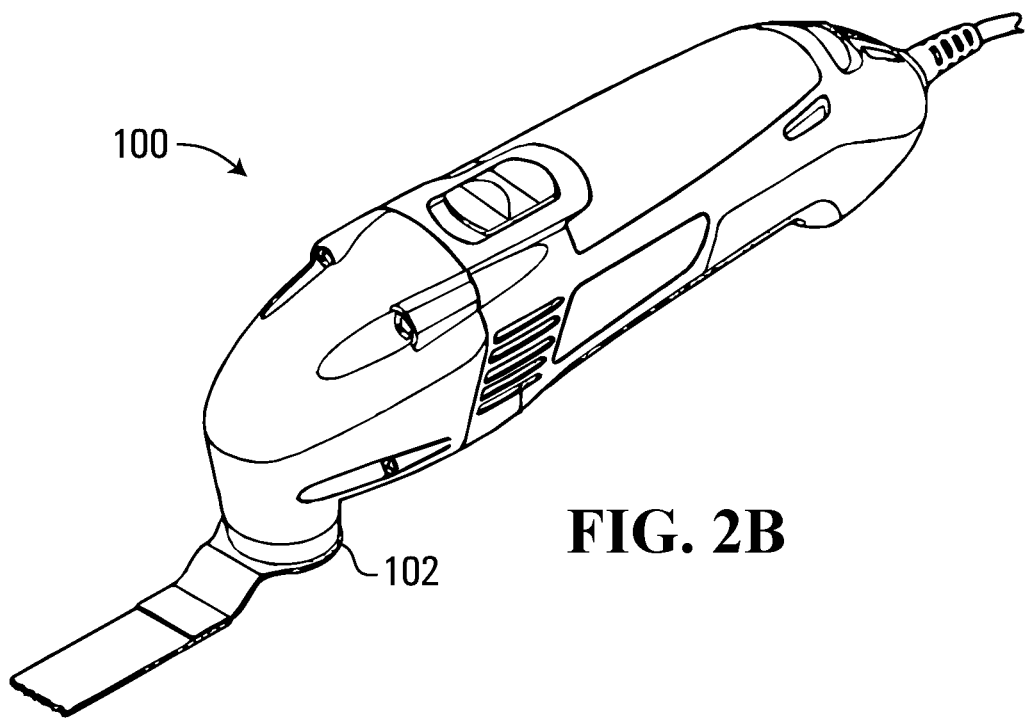
Figure 3:
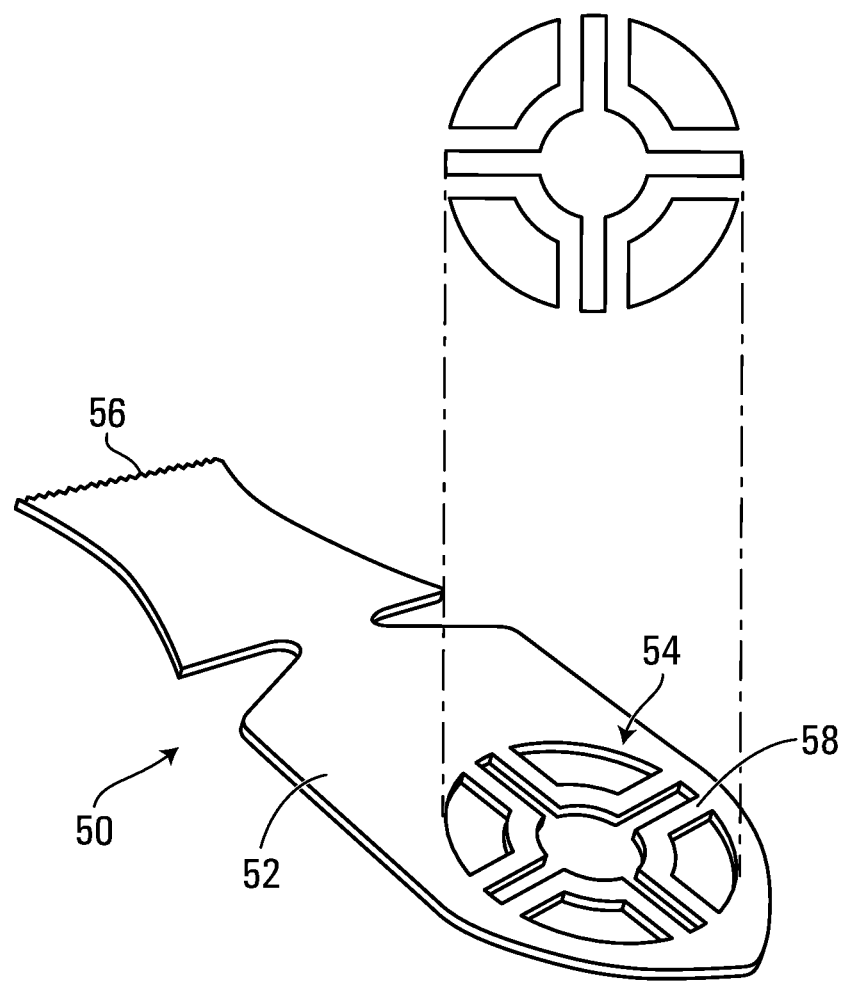
FIG. 3 is a perspective view of an accessory for an oscillating power tool, in this example a blade accessory, in accordance with a specific embodiment of the invention.

FIG. 3 shows an example of an accessory 50 for use with an oscillating power tool 100 in accordance with an embodiment of the invention. The oscillating power tool 100, shown in FIGS. 2A and 2B, comprises a drive flange 102 for mounting the accessory 50 thereto. In this embodiment, the accessory 50 is a blade accessory used for cutting. The blade 50 comprises a body 52 and an arbor 54 defined in the body 52 for matingly engaging attachment elements (e.g., projections) of the drive flange 102 of the oscillating power tool 100.

As will be discussed in more detail below, the blade 50 may be mounted onto oscillating power tools produced by a variety of manufacturers despite the fact that these manufacturers design the drive flanges of their oscillating power tools to have different patterns of projection in order to be solely compatible with their own accessories. Notably, as discussed above, replacement blades for manufacturers' oscillating power tools are only provided by those manufacturers for use with their specific oscillating power tool and could not be used with other manufacturers' oscillating power tools.

As discussed above, this common practice can result in users being required to hold stock of each individual oscillating power tool's requisite replacement blades due to an arbor (i.e., a fitting slot/hole) of the accessory that is unique to each manufacturer's oscillating power tool. This results in higher cost and higher blade inventories than what could be allowed under a "universal" arbor (i.e., an arbor that is compatible with a multitude of manufacturers' oscillating power tools).

Continuing with FIG. 3, the body 52 of the blade 50 extends in a longitudinal direction from a first end 56 to a second end 58. The first end 56 of the body 52 is a functional end that allows the accessory 50 to perform its function (i.e., cutting). As such, in this embodiment, the first end 56 is a blade end that allows the blade 50 to cut. For instance, in this example, the blade end 56 comprises cutting teeth. The second end 58 is an attachment end for mounting the blade 50 to the drive flange 102 of the oscillating power tool 100. More specifically, the attachment end 58 defines the arbor 54 which is configured to matingly engage attachment elements (e.g., projections) of the drive flange 102 of the oscillating power tool 100.

The body 52 of the blade 50 is made of a material 62. The material 62 may be, for example, a metallic material, a plastic material or any other suitable material.

The arbor 54 can be thought of as being "universal" as it is compatible, with no loss of functionality, with the drive flanges (sometimes referred to as "receptacles") of the oscillating power tools of multiple manufacturers.

Figure 4:
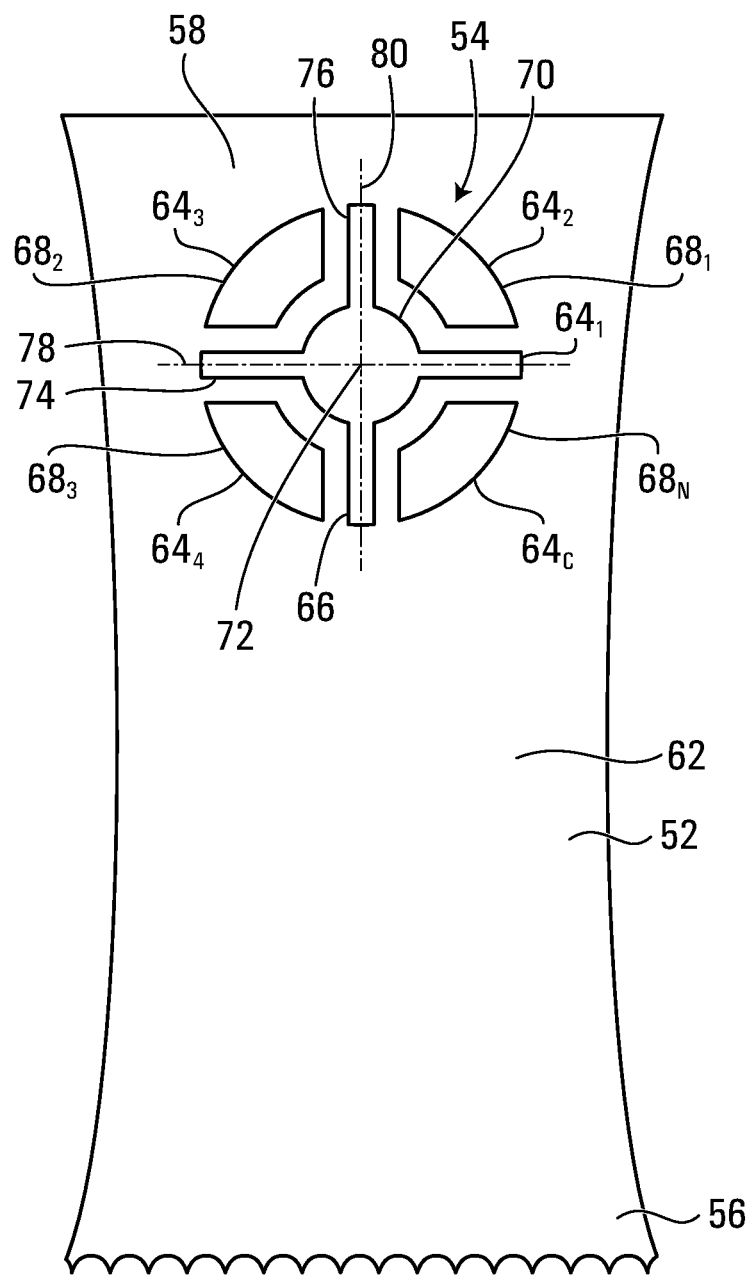
FIG. 4 is a front view of another example of a blade m accordance with another embodiment of the invention.

To that end, and as can best be seen in FIG. 4, the arbor 54 comprises a plurality of cavities $64_1$-$64_c$ which are configured to receive the attachment elements of the drive flange 102 of the oscillating power tool 100. In this embodiment, the plurality of cavities $64_1$-$64_c$ includes a primary cavity 66 which is centrally located amongst the plurality of cavities $64_1$-$64_c$, and a set of secondary cavities $68_1$-$68_N$ positioned radially about the primary cavity 66. In this embodiment, the cavities $64_1$-$64_c$ are in the form of openings in that they traverse the body 52 of the blade 50 from one face of the blade 50 to another. However, in other embodiments, the cavities $64_1$-$64_c$ may be depressed or raised portions of the body 12 (e.g., debossed or embossed portions).

The primary opening 66 comprises a central opening 70 which defines a central axis 72 of the arbor 54, and first and second elongated openings 74, 76 each conjoined with the central opening 70 and extending radially from the central axis 72. More particularly, the first elongated opening 74 extends from the central axis 72 along a first radial axis 78 while the second elongated opening 76 extends from the central axis 72 along a second radial axis 80 transversal to the first radial axis 78. In particular, the second radial axis 80 is substantially orthogonal to the first radial axis 78. The primary opening 66 may thus be considered to be generally cross-shaped with a generally circular opening located at the intersection of the two arms of the cross. Moreover, in this embodiment, the second radial axis 80 lies along the longitudinal direction of the body 52 of the blade 50.

Characteristics of the cavities of the arbour 54 may be better appreciated with reference to FIG. 5. As depicted, the first and second elongated openings 74, 76 are generally rectangular and each has a width $W_E$ of about 2 mm measured in a direction normal to the first and second radial axes 78, 80. Moreover, each of the first and second elongated openings 74, 76 extends from the central opening 70 by a length $L_E$ of about 7.5 mm. For its part, the central opening 70 has a generally circular shape which defines an inner circle 75 of the arbor 54. The inner circle 75 has a diameter $D_{IC}$ of about 10 mm.

The secondary openings $68_1$-$68_N$ are disjoined from (i.e., not connected to) the primary opening 66 such that the material 62 of the body 52 separates the secondary openings $68_1$-$68_N$ from the primary opening 66. More particularly, at least some of the secondary openings $68_1$-$68_N$ are separated from the central opening 70 by a radial distance Ro of about 3.25 mm. Moreover, the secondary openings $68_1$-$68_N$ are positioned radially about the central axis 72 along respective radial axes $82_1$-$82_N$ distinct from the first and second radial axes 78, 80 of the first and second elongated openings 74, 76.

Figure 6G:
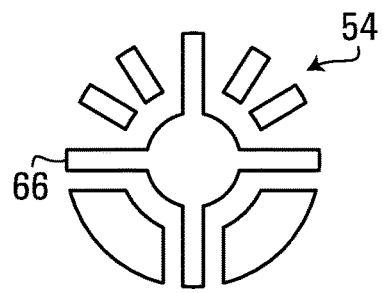
FIG. 6G shows another variant of the arbor of FIG. 4 in which the set of secondary cavities includes six secondary cavities.
Figure 6H:
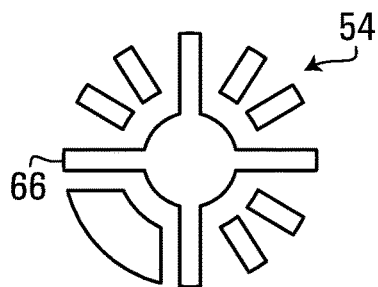
FIG. 6H shows another variant of the arbor of FIG. 4 in which the set of secondary cavities includes seven secondary cavities.
Figure 6I:
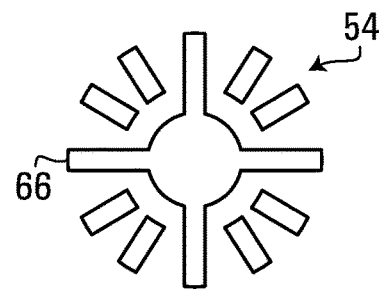
FIG. 6I shows another variant of the arbor of FIG. 4 in which the set of secondary cavities includes eight secondary cavities.
Figure 6J:
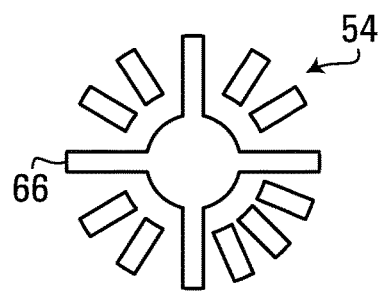
FIG. 6J shows another variant of the arbor of FIG. 4 in which the set of secondary cavities includes nine secondary cavities.
Figure 6K:
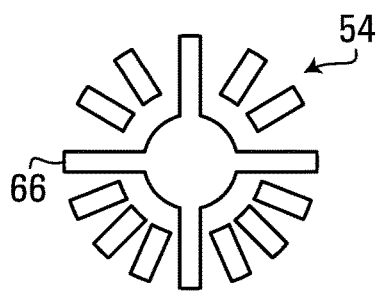
FIG. 6K shows another variant of the arbor of FIG. 4 in which the set of secondary cavities includes ten secondary cavities.
Figure 6L:
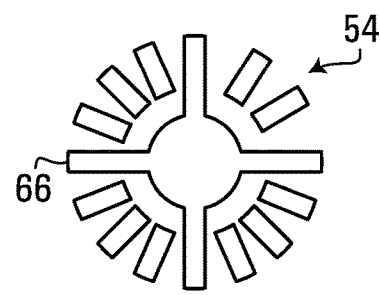
FIG. 6L shows another variant of the arbor of FIG. 4 in which the set of secondary cavities includes eleven secondary cavities.
Figure 6M:
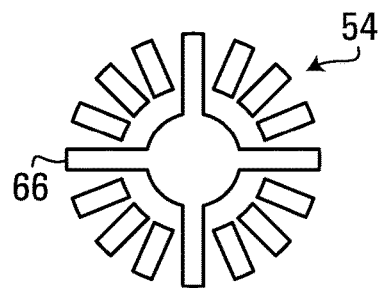
FIG. 6M shows another variant of the arbor of FIG. 4 in which the set of secondary cavities includes twelve secondary cavities.

While in the embodiments depicted in FIGS. 4 and 5, the set of secondary openings $68_1$-$68_N$ includes four secondary openings, the set of secondary openings $68_1$-$68_N$ may include more or fewer secondary openings in other embodiments as depicted in FIG. 6A to 6M. For instance, the set of secondary openings $68_1$-$68_N$ may include at least one secondary opening, in some cases at least two separate secondary openings, in some cases at least four separate secondary openings, and in some cases even more. For example, the set of secondary openings $68_1$-$68_N$ may include twelve separate secondary openings, as shown in FIG. 6M.

The primary opening 66 and the set of secondary openings $68_1$-$68_N$ form a substantially circular shape defining an outer circle 84 of the arbor 54. In specific practical implementations, the outer circle 84 has a diameter $D_{OC}$ of about 25 mm. At least some of the secondary openings $68_1$-$68_N$ extend to define part of a periphery of the outer circle 84. As such, at least some of the secondary openings $68_1$-$68_N$ have a radial extent $R_E$ of about 4.25 mm.

The blade accessory 50, via the configuration of its arbor 54, notably its openings $64_1$-$64_C$, is compatible with the major manufacturers' oscillating power tools with no loss of functionality at a price that will allow for replacement of dulling blades when required, as opposed to stretching the use of manufacturers' blades beyond a point of usefulness (i.e., after they've become dull) due to their cost. In connection with the specific design depicted in FIG. 5, the arbor 54 may allow the blade 50 to be placed at angles up to every 30 degrees in a circle when mounted onto the drive flange of may oscillating power tools.

Looking to FIG. 5, and in a specific implementation, the arbor 54 of the blade accessory has the following dimensions, expressed within a range of greater than or less than 1 mm for all measurements:

A) Outer circle 84 diameter $D_{OC}$: 25 mm
B) Inner circle 75 diameter $D_{IC}$: 10 mm
C) Radius distance from outer limit of middle circle to outer circle $R_E$: 4.25 mm
D) Primary opening 66: first (x-axis) —78: 25 mm, second (y-axis) 80: 25 mm, 2 mm width ($W_E$)
E) Radial distance $R_D$ between central opening 70 and secondary openings $68_1$-$68_N$: 3.25 mm It will be understood that while the accessory 50 has been described and shown as a blade accessory in this embodiment, in other embodiments, the accessory 50 may be a rasp, a sander, a scraper, a grout remover or any other accessory for oscillating power tools in any material such as metal, plastic, or other. For example, the functional end 56 of the accessory 50 can serve as either a blade to cut, a sander to sand, a rasp to sand, a scraper to scrape, or a grout remover to remove grout with power assistance from the oscillating power tool. In specific practical implementations, the accessory 50 may be configured to fit tightly onto the flange 102 of the oscillating power tool 100 to provide functionality, maintain torque, and is secured by the arbor 54, and a screw or fastener on the other side of the drive flange 102 of the oscillating power tool 100.

The above specification, and examples provide a complete description of the use of the invention. Since many embodiments of the invention can be made without departing from the spirit and scope of the invention, the invention is defined by the claims.

The invention claimed is:

1. An accessory for an oscillating power tool comprising:
a body with an arbor for attaching to the oscillating power tool, the arbor comprising:
a first primary opening extending along a latitudinal axis of the accessory from a central opening to a first radial distance from a central axis of the arbor;
a second primary opening extending along a longitudinal axis of the accessory from the central opening to the first radial distance;
a third primary opening extending along the latitudinal axis from the central opening to the first radial distance;
a first set of secondary openings disjoined from the central opening and disposed between the first and second primary openings; and
a second set of secondary openings disjoined from the central opening and disposed between the second and third primary openings;
wherein the arbor is configured to receive a plurality of protruding drive elements from the oscillating power tool; and
wherein the first set of secondary openings and second set of secondary openings do not extend beyond the first radial distance.

2. The accessory of claim 1, wherein the first set of secondary openings consists of two openings and the second set of secondary openings consists of two openings.

3. The accessory of claim 2 wherein the arbor further comprises a third set of secondary openings disjoined from the central opening and disposed between the first and third primary openings, wherein the third set of secondary openings consists of two openings.

4. The accessory of claim 3, wherein the second primary opening lies along an axis that bisects the accessory.

5. The accessory of claim 4 wherein the primary openings have a width of about 2 mm.

6. The accessory of claim 4 wherein the first radial distance is about 12.5 mm.

7. The accessory of claim 1 wherein the arbor is a universal arbor.

8. The accessory of claim 1 wherein the arbor further comprises a fourth primary opening extending along the longitudinal axis from the central opening to the first radial distance.

9. The accessory of claim 8 wherein the arbor further comprises a third set of secondary openings disjoined from the central opening and disposed between the first and fourth primary openings and a fourth set of secondary openings disjoined from the central opening and disposed between the third and fourth primary openings.

10. The accessory of claim 9 wherein the third set of secondary openings consists of two openings and the fourth set of secondary openings consists of two openings.

11. An accessory for an oscillating power tool comprising:
a body with an arbor for attaching to the oscillating power tool, the arbor comprising:
a first primary opening extending from a central axis of the arbor outward along a portion of a latitudinal axis of the accessory;
a second primary opening extending from the central axis of the arbor outward along a portion of a longitudinal axis of the accessory, wherein the second primary opening extends to the same distance from the central axis as the first primary opening;
a third primary opening extending from the central axis of the arbor outward along a portion of the latitudinal axis, wherein the third primary opening extends to the same distance from the central axis as the first primary opening;
a first secondary opening disjoined from the first and second primary openings and disposed between the first and second primary openings; and
a second secondary opening disjoined from the first and second primary openings and disposed between the second and third primary openings;
wherein the arbor is configured to receive a plurality of protruding drive elements from the oscillating power tool;
wherein the first secondary opening and second secondary opening do not extend beyond the distance that the first primary opening extends from the central axis.

12. The accessory of claim 11, further comprising a third secondary opening disjoined from the first and second primary openings and disposed between the first and second primary openings and a fourth secondary opening disjoined from the second and third primary openings and disposed between the second and third primary openings.

13. The accessory of claim 12 wherein the arbor further comprises a fifth secondary opening and a sixth secondary opening disjoined from the first and third primary openings and disposed between the first and third primary openings.

14. The accessory of claim 13, wherein the second primary opening lies along an axis that bisects the accessory.

15. The accessory of claim 11, wherein at least one of the secondary openings is elongated radially from the central axis of the arbor, and further comprises a rounded end that is distal to the central axis of the arbor and a rounded end that is proximal to the central axis of the arbor.

16. An accessory for an oscillating power tool comprising:
a body with an arbor for attaching to the oscillating power tool, the arbor comprising:
a first primary opening extending along a latitudinal axis of the accessory from a central opening defining a central axis of the arbor to a first radial distance;
a second primary opening extending along a longitudinal axis of the accessory from the central opening to the first radial distance;
a third primary opening extending along the latitudinal axis from the central opening to the first radial distance;
a first secondary opening disposed between the first and second primary openings; and
a second secondary opening disposed between the second and third primary openings,
wherein the first and second secondary openings do not extend beyond the first radial distance;
wherein the arbor is configured to receive a plurality of protruding drive elements from the oscillating power tool.

17. The accessory of claim 16, wherein the arbor further comprises a third secondary opening disposed between the first and second primary openings and a fourth secondary opening disposed between the second and third primary openings.

18. The accessory of claim 17 wherein the arbor further comprises a fifth secondary opening and a sixth secondary opening, the fifth and sixth secondary openings disjoined from the central opening and disposed between the first and third primary openings.

19. The accessory of claim 18, wherein the second primary opening lies along an axis that bisects the accessory.

20. The accessory of claim 19 wherein the first radial distance is about 12.5 mm.

\* \* \* \* \*